US007244607B2

(12) United States Patent
Martin et al.

(10) Patent No.: US 7,244,607 B2
(45) Date of Patent: Jul. 17, 2007

(54) CHROMOBACTERIUM SUBTSUGAE SP. NOV. FOR CONTROL OF INSECT PESTS

(75) Inventors: Phyllis A. W. Martin, Lanham, MD (US); Ashaki D. S. Shropshire, Washington, DC (US); Dawn E. Gundersen-Rindal, Silver Spring, MD (US); Michael B. Blackburn, Woodbine, MD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 369 days.

(21) Appl. No.: 10/678,023

(22) Filed: Oct. 1, 2003

(65) Prior Publication Data

US 2005/0074431 A1    Apr. 7, 2005

(51) Int. Cl.
*C12N 1/20* (2006.01)
(52) U.S. Cl. .................................. 435/252.1; 424/93.4
(58) Field of Classification Search ...................... None
See application file for complete search history.

(56) References Cited

U.S. PATENT DOCUMENTS 5,428,175 A * 6/1995 Hoshino et al. ............ 548/455

OTHER PUBLICATIONS

Martin, P.A.W., and Blackburn, M., "Bacterial Strains Lethal to Colorado Potato Beetle Larvae," (May 2001) *American Society for Microbiology 101st General Meeting*.

Martin, P.A.W., and Shropshire, A. "Survival of *Chromobacterium voilaceum*, An Insect Pathogen, Under Various Conditions," (May 2002) *American Society for Microbiology 102nd General Meeting*.
Martin, P.A.W., "An *In Vitro* Inhibition Test that Predicts Toxicity of Bacterial Pathogen Combinations in the Colorado Potato Beetle," *Biocontrol Science and Technology* (2002) 12:643-647.
Martin, P.A.W., "A Freeze-Dried Diet to Test Pathogens of Colorado Potato Beetle," (2004) (available at www.sciencedirect.com on Jul. 30, 2003) *Biological Control* 29:109-114.
Martin, P.A.W., Blackburn, M., and Gundersen-Rindal, D., "Characterization of *Chromobacterium sp.*, a Purple Bacterium Toxic to Insects," (May 2003) *ASM 103rd General Meeting*, Washington D.C. Q-226, p. 555.
Martin, P.A.W., Shropshire, A.D.S., Romani, H., "A Method to Detect Viable, Pigmented Insect Pathogens from Soil," (May 2003) *ASM 103rd General Meeting, Washington D.C.* Q-436, p. 593.
Martin, P.A.W., and Schmidtmann, E.T., "Isolation of Aerobic Microbes from *Ixodes scapularis* (Acari: Ixodidae), the Vector of Lyme Disease in the Eastern United States," *Biological and Microbial Control* (1998) 91(4):864-868.
Brazilian National Genome Project Consortium, "The Complete Genome Sequence of *Chromobacterium violaceum* reveals remarkable and exploitable bacterial adaptability," (Sep. 30, 2003) *Proc. Natl. Acad. Sci.* 100(20) 11660-11665.

* cited by examiner

*Primary Examiner*—Irene Marx
(74) *Attorney, Agent, or Firm*—Howard V. Owens; Margaret A. Connor; John D. Fado (57) ABSTRACT

*Chromobacterium suttsuga* sp. nov., a new species of the genus *Chromobacterium* which possesses insecticidal activity, is described. The invention also relates to insecticidally-active metabolites obtained from the strain and to insecticidal compositions comprising cultures of the strain and/or supernatants, filtrates, and extracts obtained from the strain, and use thereof to control insect pests.

3 Claims, 3 Drawing Sheets

SEQUENCE LISTING

```
<160> NUMBER OF SEQ ID NOS: 3

<210> SEQ ID NO 1
<211> LENGTH: 1440
<212> TYPE: DNA
<213> ORGANISM: Chromobacterium suttsuga NRRL B-30655

<400> SEQUENCE: 1
tggagagttt gatcctggct cagattgaac gctggcggca tgctttacac atgcaagtcg 60
aacggtaaca gggtgcttgc accgctgacg agtggcgaac gggtgagtaa tgcgtcggaa 120
tgtaccgtgt aatgggggat agctcggcga aagccggatt aataccgcat acgccctgag 180
ggggaaagcg ggggatcgaa agacctcgcg ttatacgagc agccgacgtc tgattagcta 240
gttggtgagg taagagctca ccaaggcgac gatcagtagc gggtctgaga ggatgatccg 300
ccacactggg actgagacac ggcccagact cctacgggag gcagcagtgg ggaattttgg 360
acaatggggg caaccctgat ccagccatgc cgcgtgtctg aagaaggcct tcgggttgta 420
aaggactttt gtcagggagg aaatcccgct ggttaatacc cggcggggat gacagtaccb 480
gaagaataag caccggctaa ctacgtgcca gcagccgcgg taatacgtag ggtgcaagcg 540
ttaatcggaa ttactgggcg taaagcgtgc gcaggcggtt ttgcaagtct gatgtgaaag 600
ccccgggctc aacctgggaa cggcattgga gactgcaaga ctagagtgcg tcagaggggg 660
gtagaattcc gcgtgtagca gtgaaatgcg tagagatgcg gaggaatacc gatggcgaag 720
gcagccccct gggatgacac tgacgctcat gcacgaaagc gtggggagca aacaggatta 780
gataccctgg tagtccacgc cctaaacgat gtcaattagc tgttgggggt ttgaatcctt 840
ggtagcgtag ctaacgcgtg aaattgaccg cctggggagt acggccgcaa ggttaaaact 900
caaaggaatt gacggggacc cgcacaagcg gtggatgatg tggattaatt cgatgcaacg 960
cgaaaaacct tacctgctct tgacatgtac ggaacttggt agagatatct tggtgcccga 1020
```

-continued

```
aagggagccg taacacaggt gctgcatggc tgtcgtcagc tcgtgtcgtg agatgttggg   1080
ttaagtcccg caacgagcgc aacccttgtc attagttgcc atcatttagt tgggcactct   1140
aatgagactg ccggtgacaa accggaggaa ggtggggatg acgtcaagtc ctcatggccc   1200
ttatgagcag ggcttcacac gtcatacaat ggtcggtaca gagggtcgct aagccgcgag   1260
gtggtgccaa tctcataaaa ccgatcgtag tccggatcgc actctgcaac tcgagtgcgt   1320
gaagtcggaa tcgctagtaa tcgcagatca gcatgctgcg gtgaatacgt tcccgggtct   1380
tgtacacacc gcccgtcaca ccatgggagt gagtttcacc agaagtgggt aggctaaccg   1440

<210> SEQ ID NO 2
<211> LENGTH: 23
<212> TYPE: DNA
<213> ORGANISM: Chromobacterium suttsuga NRRL B-30655

<400> SEQUENCE: 2
aacgctggcg gcatgcttta cac                                              23

<210> SEQ ID NO 3
<211> LENGTH: 19
<212> TYPE: DNA
<213> ORGANISM: Chromobacterium suttsuga NRRL B-30655

<400> SEQUENCE: 3
gaggaaatcc cgctggtta                                                   19
```

CHROMOBACTERIUM SUBTSUGAE SP. NOV. FOR CONTROL OF INSECT PESTS

BACKGROUND OF THE INVENTION

1. Field of the Invention

The present invention relates to a new species of microorganism and use for biocontrol of insect pests. More particularly, the invention relates to a newly discovered species of *Chromobacterium* bacterium that exhibits insecticidal activity. The invention also relates to metabolites obtained from the strain that possess insecticidal activity and to insecticidal compositions comprising cultures of the novel strain and/or supernatants, filtrates, and extracts obtained from the strain, and use thereof to control insect pests.

2. Description of the Art

Many insects, in particular leaf-feeding and sucking insects, are pestiferous and are responsible for substantial crop losses and reduced crop quality worldwide. Exemplary pestiferous leaf-feeding insects include insects of the order Coleoptera (beetles) such as the Colorado potato beetle and corn rootworm. Exemplary pestiferous leaf-feeding insects in the order Lepidoptera include diamondback moth and gypsy moth. Exemplary pestiferous sucking insects include insects of the *Bemisia* genus, in particular, *Bemisia* argentifolii Bellows & Perring (silverleaf whitefly).

The Colorado potato beetle (Chrysomelidae: *Leptinotarsa decemlineata* (Say)) is found throughout most of North America and is a major insect pest of potatoes, tomatoes, eggplant, and other solanaceous plants. Larvae and adults feed on the foliage of the host plants. Adult Colorado potato beetles overwinter in the soil and emerge in spring and establish themselves on a plant, mate, and the females lay clumps of eggs. Larvae hatch from the eggs in about 4 to 15 days, and the insect can go from egg to adult in as little as 21 days. Depending on the geographic location of the pest in North America, the Colorado potato beetle can complete one to three generations per year.

Control of the Colorado potato beetle is critical to prevent or reduce the substantial crop losses and reduced crop quality caused by this pest. Annual control of the Colorado potato beetle on potatoes, tomatoes, and eggplant is about $115 million. Of serious concern is the fact that the Colorado potato beetle has developed resistance to almost every chemical insecticide used against it and is showing signs of resistance to *B. thuringiensis*. The average of a chemical control agent in the field before resistance begins to develop is estimated to be 3.5 years. Additional means to control this pest are needed as well as an alternative to *B. thuringiensis* for organic producers.

The corn rootworm (Chrysomelidae: *Diabrotica* spp.) are leaf beetles that feed predominantly on corn. The larvae cause the most significant damage through feeding injury to the corn root. Adult corn rootworm beetles can also cause substantial foliar injury and interfere with pollination. Control of corn root worm is very expensive with some estimates reaching $1 billion. The Western corn rootworm (*Dibrotica virgifera virgifera*) has been cited as the most destructive pest of continuous corn in the United States today. Treatment expense and crop losses from the Western corn rootworm cost U.S. producers more than $1 billion annually. Additional control measures are needed to control this serious agricultural pest.

The diamondback moth (Lepidoptera: Plutellidae: *Plutella xyostella* L.) is one of the most widespread lepidopteran pests on vegetable *brassica* crops world wide, causing annual losses in the order of $1 billion. Host plants include virtually all cruciferous vegetable crops, including broccoli, cabbage, and cauliflower. Similar to the Colorado potato beetle, the diamondback moth is resistant to many pesticides, including, in some cases, *B. thuringiensis*. Alternative control, particularly organically based pesticides, is needed for this serious agricultural pest.

Whiteflies [Homoptera/Hemiptera] are found worldwide in tropical and subtropical areas as well as temperate zones. They are plant feeders, with piercing-sucking mouth parts that penetrate leaf tissue and puncture the plant leaf veins and withdraw plant sap. Economic losses and plant pest status occurs as a result of plant feeding and reduced crop yields, transmission of plant-infecting viruses, and product contamination from excreted honeydew. Whiteflies are characterized by high reproductive rates, logarithmic population growth, multiple plant hosts, and dispersal within and between plant hosts in response to plant senescence, wind, and other factors. Their habitats are found within and around field crops such as cotton and cultivated vegetables. There are at least 37 species identified in the *Bemisia* genus. *Bemisia tabaci* (Gennadius) (Homoptera/Hemiptera: Aleyrodidae) is one of the most serious economic pests attacking over 300 species of plants. The silverleaf whitefly, *Bemisia argentifolii* Bellows & Perring, is an even more serious pest, attacking as many as 500 different hosts. These include commercially grown crops as well as ornamentals and many alternative weed hosts. Recently, the silverleaf whitefly has also been reported to be present in greenhouses. In addition, the silverleaf whitefly is more prolific than *B. tabaci*. In the U.S., damage due to just one species of whitefly, the silverleaf whitefly, has been estimated at $500 million. Poinsettia is one of its favorite targets. According to the Nursery Men and Landscapers Association, the nursery and greenhouse industry in 1997 was a ten billion dollar industry. Because the silverleaf whitefly attacks commercially grown crops as well as ornamentals and many weed hosts, it is particularly difficult to control. For example, in the irrigated desert crop-growing areas of Arizona and California, sequential planting of cole crops, curcurbits, cotton, and alfalfa offers a continuum of year-round susceptible host material and the opportunity for whiteflies to move within and among cropping systems to expand population development. Whiteflies are difficult to control with insecticides, and have developed resistance to some pesticides. Therefore, additional control methods for whiteflies are needed.

Biological control agents (biopesticides) can be an important addition or alternative to control using synthetic chemical pesticides and important in integrated pest management. Many factors are involved in a successful microbial control agent, including survival in the environment, mode of entry in the gut, and replication in the insect. Although some microbes (e.g., *Bacillus thuringiensis* Berliner) kill by toxins, the replicating organism also contributes to the overall control of the insect (Schnepf et al. 1998).

Strains of bacterial species that kill insects have been reported. *Paenibacillus popilliae* was the first bacterial pesticide (Milky Spore) to successfully control pest insects (Japanese beetles; Dutky, 1940). Various strains of *B. thuringiensis* are toxic to other scarab beetles (Ohba et al., 1992), *Diabrotica* spp. (Tailor et al., 1992), caterpillars, beetles, and mosquitoes (Schnepf et al., 1998). *Bacillus thuringiensis* has been used for control of the Colorado potato beetle as a foliar spray (Ferro et al., 1997) or in transgenic plants (Perlak et al., 1993). Heins et al., U.S. Pat. Nos. 6,417,163 and 6,291,426, report compositions and methods for controlling plant pests including the Colorado potato beetle using a novel strain of *Bacillus subtilis*, AQ713. *Serratia entomophila* and *Serratia proteamaculans* (Jackson et al., 1993) cause amber disease in grass grubs and are being developed in New Zealand. *Photorhabdus luminescens*, with nematodes as a vector, has been described as pathogenic to Lepidoptera (Forst and Nealson, 1996). High molecular weight protein complexes isolated from *P. luminescens* are toxic to lepidopteran and coleopteran insects (Bowen et al., 1998; Guo et al., 1999). One of these complexes, Tca, has been shown to disrupt the midgut epithelium of tobacco hornworm larvae (Blackburn et al., 1998).

Many bacterial insect pathogens are not toxic enough for field control. Other than *B. thuringiensis* as discussed above, few other bacteria have been used to effectively control Colorado potato beetles (Onstad, 2001). Pathogens such as *Serratia marcescens* Bizo (Grimont & Grimont, 1978) or Spiroplasma leptinotarsae Hackett et al. (Hackett et al., 1996) while causing mortality of beetles in the lab, do not effectively control this pest in the field.

Successful fungal biocontrol agents for the Colorado potato beetle pest include *Beauveria bassiana* which has been the most successful in some areas such as Europe and the northern United States and under certain conditions such as early season applications in Virginia requiring high humidity and low temperatures (Groden and Lockwood, 1991; Poprawski et al., 1997; Martin et al., 1999).

Purple bacteria (Chromobacterium violaceum) have infrequently been isolated from insects, and have not been previously considered an insect pathogen (Bucher, 1981). This species of bacteria has been isolated from the digestive tract of the larger grain borer (Prostephanus truncatus) where they may be involved in cellulose digestion in this insect (Vazquez-Artista et al., 1997) forming a symbiotic rather than a pathogenic association. However, *C. violaceum* is mainly known for its production of a purple pigment, violacein, which has anti-microbial activity against Gram-positive and Gram-negative bacteria (Duran et al., 1983) and *Trypanosoma cruzi* (Duran et al., 1994).

SUMMARY OF THE INVENTION

We have discovered a new species of *Chromobacterium* bacterium which is distinct from all other described species in the genus and which exhibits insecticidal activity. We have designated it as *Chromobacterium subtsugae* sp. nov. A biologically pure culture of *Chromobacterium subtsugae* sp. nov. has been deposited with the Agricultural Research Service Culture Collection (NRRL) under the provisions of the Budapest Treaty on the International Recognition of the Deposit of Microorganisms for the Purpose of Patent Procedure and has been given the accession number NRRL B-30655.

The unique strain of the invention, also denoted as *Chromobacterium subtsugae* NRRL B-30655, exhibits effective insecticidal activity, and cultures of the new bacterium are useful for control of insect pests. By way of comparison, the purple type strain of *Chromobacterium violaceum* (ATCC 12472) is not toxic to insects.

The unique strain of the invention produces one or more active metabolites that possess insecticidal activity. Toxicity is released into the supernatant obtained from the strain; viable bacterial cells are not required for insecticidal activity. Accordingly, the present invention is also directed to insecticidally active supernatants and filtrates obtained from the unique strain. The one or more toxic metabolites show heat stability and protease resistance. Extracts of the strain also exhibit insecticidal activity, and the invention is further directed to insecticidally active extracts obtained from the strain of the invention.

The full length *Chromobacterium subtsguae* sp. nov. 16S rDNA gene sequence has been obtained and is given in SEQ ID NO:1. The invention is also directed to *Chromobacterium* strains which have a 16S rDNA gene sequence of SEQ ID NO:1. Such strains may be isolated for example using primers chromo 16SF1 (SEQ ID NO:2) and chromo 16SF2 (SEQ ID NO:3) and identified using the full length 16S rDNA gene sequence (SEQ ID NO:1).

The present invention is further directed to methods of controlling insects using the unique bacterium of the invention. This aspect includes application of an effective insect control amount of the strain cells, supernatant, filtrate or extract containing an insecticidally active metabolite produced by the strain or combinations thereof. *Chromobacterium subtsugae* NRRL B-30655 and/or a metabolite obtained from NRRL B-30655 has been shown to be toxic to Colorado potato beetle, corn rootworm, diamondback moth, and silverleaf whiteflies, and to have a sublethal effect on gypsy moth.

A further aspect of the invention pertains to compositions which incorporate the strain of the invention and/or compositions comprising an insecticidally active metabolite produced by the strain of the invention. Such compositions include, for example, whole cultures or suspensions of the strain; supernatants, filtrates or extracts obtained from the strain or combinations of the foregoing. Such compositions may optionally include other ingredients such as an agricultural carrier, insect feeding stimulant, spreading agent, sticking agent, thickener, emulsifier, stabilizer, preservative, pheromones, other attractants, fungicides, other insecticidal toxicants including other microbes and/or their metabolites, buffer, water, diluent or other additive as known in the art of formulation of insecticidal compositions. The bacterial biocontrol agent of the present invention may also be used in combination with chemical compounds, including for example feeding stimulants, photoactive dyes, fluorescent brighteners (also denoted as optical brighteners), fungicides, and other insecticides. Photoactive dyes in combination with biological control agents are described by Martin et al., 1998. Fluorescent brighteners, particularly those which provide protection for pathogens from the damaging effects of exposure to UV radiation and which may enhance biological activity of the organism, are described in U.S. Pat. No. 5,124,149 to Shapiro et al. The compositions are applied as known in the art to protect plants from insect pests, including for example, application to soil in a field or surrounding a plant, to target plants, e.g, plant roots, on plant foliage, stems, flowers, tubers, seedlings, and seeds. The strain on the invention can be grown on rice grains, and the rice grains applied to the plant or soil.

The invention provides a new control means against agriculturally important pestiferous insects such as the Colorado potato beetle, and gives growers alternatives to *B. thuringiensis*, as well as chemicals, for control of this and other pestiferous insects. Expanded use of biologicals for the control of the Colorado potato beetle and other insect pests will improve resistance management, reduce pesticide use, and produce novel compounds for potential use in transgenic plants. Because the new strain of the invention is a Gram-negative bacterium, it is unlikely to have mechanisms similar to *B. thuringiensis* for killing, and could be employed in resistance management.

In accordance with our discovery, it is an object of the invention to provide a biologically pure culture of a new species of *Chromobacterium*. In one aspect, the invention is directed to *Chromobacterium subtsugae* sp. nov. and strains having the identifying characteristics of NRRL B-30655 and use thereof as biological control agents against insect pests. In another aspect, the invention is directed to *Chromobacterium* strains which have a 16S rDNA gene sequence of SEQ ID NO:1.

Another object of the invention is the provision of an insecticidally active metabolite obtained from *Chromobacterium subtsugae* sp. nov.

A further object of the invention if the provision of methods for biologically controlling insect pests using the strain of the invention, an insecticidally-active metabolite obtained from the strain, and agricultural compositions which incorporate the strain or an insecticidally-active metabolite obtained from the strain.

Other objects and advantages of the invention will become readily apparent from the ensuing description.

BRIEF DESCRIPTION OF THE DRAWINGS

FIG. 1 shows the phylogenetic tree constructed by parsimony (PAUP version 4.0b, D. Soffored) analysis of nearly full-length 16S rDNA sequences from representative chromobacteria and other beta proteobacteria. Sequences were aligned with Clustal version V (DNAStar Lasergene Software, Madison, Wis.). *Escherichia coli* strain K-12 (U00096) was employed as the out-group to root the tree. Bar length represents 50 inferred character state changes. Branch lengths are proportional to the number of inferred character state transformations. Bootstrap values greater than 50 (measures of support for the inferred subclades) are shown on branches. GenBank accession numbers of the taxa are as follows: *Achromobacter xylosoidans* (M22509); *Alcaligenes faecalis* (M22508); *Burkholderia cepacia* (M22518); *Chromobacterium violaceum* ATCC 12472 (M22510); *Chromobacterium* sp. MBIC3901 (AB017487); *Eikenella corrodens* ATCC 23834 (M22512); *Iodobacter fluviatile* (M22511); *Kingella denitrificans* (M22516); *Kingella kingae* (M22517); *Vitreoscilla stercoraria* (M22519) and *Vogesella indigofera* (U45995).

FIG. 2 shows a comparison of mortality of bacterial cultures of the strain of the invention *Chromobacterium subtsugae* NRRL B-30655, *B. thuringiensis* NTEN3-2, and a water control. Single plates of each bacteria were harvested identically. The number of bacteria applied per diet pellet was $2.54\times10^8$ for *Chromobacterium subtsugae* NRRL B-30655 and $2.3\times10^8$ for NTEN3-2 (*B. thuringiensis*). Shaded bars are the time post treatment.

FIG. 3 shows the effect of age of culture of *Chromobacterium subtsugae* NRRL B-30655 on mortality of 2nd instar Colorado potato beetle larvae. The number of viable bacteria applied per diet pellet was 24 h—$1.23\times10^8$, 48 h—$2.55\times10^8$, 72 h—$5.64\times10^8$. Shaded bars are the time post treatment.

BRIEF DESCRIPTION OF THE SEQUENCE

SEQ ID NO:1 is *Chromobacterium subtsugae* sp. nov. 16S rDNA gene sequence.

SEQ ID NO:2 shows the chromo 16SF1 primer.

SEQ ID NO:3 shows the chromo 16SF2 primer.

Definitions

Unless defined otherwise, all technical and scientific terms used herein have the meaning commonly understood by a person skilled in the art to which this invention belongs. The following references provide one of skill with a general definition of many of the terms used in this invention: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., Rieger, R., et al. (eds.), Springer Verlag (1991); and Hale & Marham, THE HARPER COLLINS DICTIONARY OF BIOLOGY (1991); Sambrook et al., *Molecular Cloning—A Laboratory Manual* ($2^{nd}$ ed.) Vol. 1–3, Cold Spring Harbor Laboratory, Cold Spring Harbor Press, NY (1989); Sneath, P. H. A., Genus *Chromobacterium* Bergonzini, In: *Bergey's Manual of Systematic Bacteriology* (D. H. Bergey, J. G. Holt, and N. R. Krieg, Eds), Vol 1. pp. 580–582. Williams & Wilkins, Baltimore (1984); Atlas, R. M., *Handbook of Microbiological Media*, Boca Raton: CRC Press, Inc. (1997).

To facilitate understanding of the invention, a number of terms are defined below.

The term "whole broth culture" refers to a liquid culture containing both cells and media. If bacteria are growth on a plate the cells can be harvested in water or other liquid, whole culture.

The term "supernatant" refers to the liquid remaining when cells grown in broth or are harvested in another liquid from an agar plate and are removed by centrifugation, filtration, sedimentation, or other means well known in the art.

The term "filtrate" refers to liquid from a whole culture that has passed through a membrane.

The term "extract" refers to liquid substance removed from cells by a solvent (water, detergent, buffer) and separated from the cells by centrifugation, filtration or other method.

The term "metabolite" refers to a compound, substance or byproduct of a fermentation of a microorganism, or supernatant, filtrate, or extract obtained from a microorganism that has insecticidal activity.

The term "insecticidal activity" means that a substance has a detrimental effect on an insect, including but not limited to killing a target insect, increasing mortality, or inhibiting the incidence, growth, development or reproduction of a target insect.

DETAILED DESCRIPTION OF THE INVENTION

The present invention is directed to a newly discovered species of *Chromobacterium* bacterium which is distinct from all other described species in the genus and which exhibits insecticidal activity. We have designated it as *Chromobacterium subtsugae* sp. nov. The invention is also directed to supernatants, filtrates or extracts obtained from the strain and which include an insecticidally-active metabolite. The invention also encompasses compositions comprising the foregoing and use thereof for control of insect pests. The invention also encompasses *Chromobacterium* strains which have a 16S rDNA gene sequence of SEQ ID NO:1.

The Microorganism. The unique bacterial strain of the invention, designated as *Chromobacterium subtsugae* NRRL B-30655, was isolated from soil rich in hemlock leaves from a forest in western Maryland USA. The strain was obtained in biologically pure form by dilution plating on L. A detailed description of the origin and isolation of the strain is given in Example 1, below. *Chromobacterium subtsugae* is a member of Bacteria; Proteobacteria; Betaproteobacteria; Neisseriales; Neisseriaceae; *Chromobacterium.*

The identifying taxonomic characteristics of strain *Chromobacterium subtsugae* NRRL B-30655 are as follows: It is a facultatively aerobic Gram-negative bacterium. Cells are tapered rods averaging 0.67±0.007 μm wide and 2.43±0.05 μm long when grown on L-agar. Occasionally, curved cells are observed. Colonies start to form as cream colored but turn deep purple in 24–48 hours in the presence of oxygen. Colonies are smooth, regular and raised on L-agar. While growth occurs in the presence of 2% (w/v) NaCl, there is no growth in the presence of 3% (w/v) NaCl. The strain can be grown on any suitable solid or liquid bacteriological medium. An exemplary medium is L. Growth of the strain is effected under aerobic conditions at any temperature satisfactory for growth of the organism., e.g., from 10° C. to 40° C. (broadest range); preferably from 25° C. to 30° C. Sparse growth occurs in the ranges of 10–20° C. and 35–40° C. This isolate is unlike the type strain of *C. violaceum* which has a temperature optimum of 35° C. The strain of the invention grows from pH 5.0 to 9.0. The strain grows optimally at 25–30° C., pH 6–8.0 and with 0–1.5% (w/v) NaCl. The strain hydrolyzes casein, and produces a lecithinase and lipase on egg yolk agar. It is not hemolytic on sheep blood. It produces purple pigment in the presence of oxygen which has the spectral and solubility properties of violacein.

Strain *Chromobacterium subtsugae* NRRL B-30655 oxidizes amino acids including: D-alanine, L-alanine, L-alanylglycine, L-asparagine, L-aspartic acid, L-glutamic acid, L-histidine, D-serine, L-serine and L-threonine. Sugars utilized include D-glucose, D-fructose and D-trehalose. Acids used include acetic acid, lactic acid, bromosuccinic acid and propionic acid. Other compounds utilized as sole carbon sources are Tween 40, Tween 80, N-acetyl glucosamine, monomethyl succinate, inosine, glucose-1-phosphate, and glucose-6-phosphate.

The most predominant fatty acids could not be separated by GLC with the MIDI system and 41.3% was a combination of $C_{16:1}$ ω7c and iso$C_{15:0}$ 2OH. The predominant fatty acid is $C_{16:0}$. The other major fatty acids were $C_{16:0}$ (26%) and $C_{18:1}$ ω7c (11.4%). Other fatty acids were $C_{10:0}$ (4.5%). $C_{12:0}$ (4.6%), $C_{12:0}$ 2OH (2.6%), $C_{12:0}$ 3OH (4.2%), $C_{14:1}$ ω5c (0.2%), $C_{14:0}$ (2.9%) $C_{15:1}$ ω6c (0.3%), $C_{15:0}$ (1.0%), $C_{16:1}$ ω5c (0.4%), $C_{17:1}$ ω8c (0.2%) $C_{17:0}$ (0.1%).

A complete 16S rDNA gene sequence of *Chromobacterium subtsugae* sp. nov. NRRL B-30655 was obtained and is shown in SEQ ID NO:1.

The G+C content of *Chromobacterium subtsugae* NRRL B-30655 was found to be 64.51% (s.d.=±0.14%). FIG. 1 shows the phylogenetic tree constructed by parsimony (PAUP version 4.0b, D. Soffored) analysis of nearly full-length 16S rDNA sequences from representative chromobacteria and other beta proteobacteria.

In view of Bucher's (1981) claim that *C. violaceum* was not pathogenic to insects, it was surprising that the new strain of the invention killed Colorado potato beetle larvae. A previously described isolate of *C. violaceum* had no toxic effect on greater grain borer and was, in fact, implicated in cellulose digestion in the insect gut (Vazquez-Artista et al., 1997). Interestingly, the *C. violaceum* type strain (ATCC 12472) was not toxic to Colorado potato beetle under bioassay conditions identical to those used for *Chromobacterium subtsugae* NRRL B-30655 (data not shown). Therefore, it does not appear that the purple pigment, violacein, is responsible for toxicity. The purple pigment, violacein, was purified from *Chromobacterium subtsugae* NRRL B-30655 and when fed to Colorado potato beetle larvae was not toxic. Also, clear supernatants of *Chromobacterium subtsugae* NRRL B-30655 remained toxic. Unlike *Chromobacterium violaceum* which also produces a purple pigment, the unique strain of the invention is toxic to insects. As shown in Examples 4–7, below, *Chromobacterium subtsugae* NRRL B-30655 is toxic to Colorado potato beetle, corn rootworm, and diamondback moth. The strain also prevented gypsy moth larvae from gaining weight upon ingestion. It did not kill mosquito larvae. The strain of the invention produces one or more orally active insecticidal toxins. The toxin has been shown to be toxic to Colorado potato beetle larvae and adult silverleaf whiteflies.

On the basis of the foregoing characteristics as well as the phenotypic characteristics, we determined that the strain is a new species of the genus *Chromobacterium*, We designated the new strain *Chromobacterium subtsugae* sp. nov.

Statement of Deposit. A biologically pure culture of *Chromobacterium subtsugae* sp. nov. was deposited May 9, 2003 under terms of the Budapest Treaty with the Agricultural Research Service Culture Collection (NRRL) National Center for Agricultural Utilization Research, Agricultural Research Service, U.S. Department of Agriculture, 1815 North University Street, Peoria, Ill. 61604 USA and given the accession number NRRL B-30655. The microorganism deposit was made under the provisions of the "Budapest Treaty on the International Recognition of the Deposit of Microorganisms for the Purposes of Patent Procedure." All restrictions on the availability to the public of these deposited microorganisms will be irrevocably removed upon issuance of a United States patent based on this application. For the purposes of this invention, any isolate having the identifying characteristics of strains NRRL B-30655, including subcultures and variants thereof which have the identifying characteristics and activity as described herein are included.

Growth of the Strain of the Invention. The strain of the invention can be grown on any suitable solid or liquid bacteriological medium, for example, L-agar, L-broth, RM medium. An exemplary medium is L (also known as Luria medium). Growth of the strain is effected under aerobic conditions at any temperature satisfactory for growth of the organism., e.g., from 10° C. to 40° C. (broadest range); preferably from 25° C. to 30° C. Sparse growth occurs at 10–20° C. and 35–40° C. The strain grows optimally at 25–30° C., pH 6.5–8.0 and with 0–1.5% (w/v) NaCl. It does not grow on 3% NaCl. It grows from pH 5.0 to 9.0.

The recommended conditions for optimal cultivation of the strain are the following: subculture on L-agar and incubate at 25° C. for at least 48 hours for purple pigment formation. The culture is viable on laboratory media for about 7 days. It should be subcultured at least weekly.

Maintenance of Stock Cultures. The strain is maintained to keep it stable, such as storing as lyophilized preparations, frozen preparations, or by storing in glycerol at −80° C. We have also stored the culture as follows: a plate of *Chromobacterium subtsugae* NRRL B-30655 on L-agar (exact age unknown) incubated at room temperature was scraped using 10 ml sterile water. The suspension was mixed thoroughly and 2 ml placed into a vial (approximate size—3 ml) containing 5 sterile Blank Sensi-disks (paper disks). The vial now containing bacteria laden paper disks was briefly shaken and stored on the benchtop inside of a dark box. More than 11 months later we were able to recover the *Chromobacterium subtsugae* NRRL B-30655 by placing one of the paper disks on an L-agar plate and incubating at 25° C. for 48 hours. This isolate was tested against Colorado potato beetle and found to have lost no toxic activity upon extended storage by this method.

Insecticidally-active metabolite obtained from *Chromobacterium subtsugae* NRRL B-30655. The unique strain of the invention produces one of more active metabolites that are toxic to insect pests. Toxicity is released into the supernatant obtained from the strain; viable bacterial cells are not required for insecticidal activity. This demonstrated by the fact that the bacteria survive less than 24 hours in the diet pellet used to feed Colorado potato beetle larvae (see Example below), yet remain lethal to larvae. Cultures with few viable cells are comparable in toxicity to cultures with greater than $10^8$ viable cells. *Chromobacterium subtsugae* NRRL B-30655 could not be recovered consistently from dead larvae. Most directly, cell-free supernatants can retain most of the toxicity of the whole cultures. Even culture fluid that has passed through a 10 K filter retains some toxicity (10%).

To obtain the one or more insecticidally active toxic agents, the strain of the invention is grown as described above, and supernatants, filtrates, or extracts are obtain using methods know in the art. The one or more toxins are made after exponential growth ceases. For example, the strain normally grows at 25° C. and forms purple pigment in 48 hours when well aerated. This isolate is unlike the type strain of *C. violaceum* (ATCC 12472) which has a temperature optimum of 35° C. In contrast, the strain of the invention has only sparse growth above 35° C. Exemplary conditions for obtaining the one or more toxins are: growing cultures on L-agar plates for 4–5 days at 25° C. and harvesting in water. This toxicity is stable at room temperature for at least 1 month.

Stability of the Toxin. While insect toxin formation is heat sensitive, the toxin itself, after formation, is stable. For example, we have shown that the toxin is stable when: frozen, heated to 65° C. for 10 min, stored at room temperature for 28 days, and exposed to either acid (pH 2) or base (pH 9). As shown in Example below, heat treatment at 90° C. for 10 minutes generally reduced toxicity, but the extent of reduction depended on the age of the culture. Most of the one or more insecticidally active metabolites were retained by a 100 K filter. Some activity remained after passage through a 10 K filter with a fresh culture. The one or more active toxins are not recovered after filtering though a 100 Mdalton filter. These data suggest a large and stable macromolecule. Treatment of fresh cultures with an exoprotease also reduced toxicity. Without being bound by theory, it is suggested that the bacterial strain may be producing multiple toxins with varying properties, as treatment with protease or heat seems to affect some of the toxicity, especially with fresh cultures, but not all. It appears that the one or more toxins are cell associated and are released from, or are less associated with, the cells as the culture ages, or by extraction with detergents or buffers that are known to release molecules from membranes. They do not appear to be typical proteins based on their heat and acid stability. The uniqueness of the one or more toxic agents is indicated by the properties of heat stability and protease resistance. It is suggested that one of the one or more toxins is large, heat stable and associated with the cell membrane. It can be extracted with water, but more efficiently with detergents such as Triton X-100 or buffers such as CHAPS. However, there are indications that a smaller molecule that is less stable, heat labile, and susceptible to protease may also present and can be assayed from fresh cultures. In the toxicity experiments that were done immediately after harvesting cells both toxins appeared to be present, but the labile one disappeared or was converted to the stable form. However, as discussed above, stable toxin can be obtained by growing cultures on L-agar plates for 4–5 days at 25° C. and harvesting in water. This toxicity is stable at room temperature for at least 1 month.

Toxin production was genetically stable over time. As shown in the Example below, in 20 transfers in liquid culture, the $19^{th}$ transfer was as toxic as the initial culture, though the toxicity varied among transfers depending on the time of harvest. While most cultures formed the purple pigment that is indicative of *Chromobacterium*, some did not. Pigment formation was not an indicator of toxicity. The non-pigmented cultures gave rise to pigmented cultures and colonies formed when titering the liquid cultures were always purple. In a parallel experiment with a liquid medium with reduced nutrients, at the 11th transfer, some non-pigmented colonies appeared on the titer plates. Most of these colonies upon subculture quickly reverted to pigmented types. However, one mutant remained non-pigmented. Its relation to the parental strain was confirmed by fatty acid analysis of the membrane. This mutant is no longer toxic to Colorado potato beetle larvae. This non toxic mutant is useful to characterize the one or more toxins produced by strain *Chromobacterium subtsugae* NRRL B-30655.

When filter-sterilized supernatants of *Chromobacterium subtsugae* NRRL B-30655 were tested against $2^{nd}$ instar Colorado potato beetle larvae, the toxicity was dependent on the age of the culture. Cell free supernatants from cultures up to 48 hours old had only 9–20% the toxicity of the whole culture (Table 3), while the toxicity of supernatants from cultures older than 72 hours was 55–86% of whole cultures (Table 3). This confirmed previous observations that cultures older than 7 days with few viable cell counts were also toxic, however peak toxicity occurred when cell number was maximal. Filtered supernatants were clear or only slightly purple compared to whole cultures when filtered through nylon filters. Supernatants filtered through PES membranes retained their purple color.

For *Chromobacterium subtsugae* NRRL B-30655, there were no differences in toxicity of fresh filtrates that were heated to 65° C. for 10 min (60% filtrate, 61.5% heat-treated filtrate). There was a slight decrease in toxicity when fresh filtrates were treated with protease type XIV (51.7% protease-treated filtrate) compared to those filtrates that were not treated. When a fresh supernatant that caused 55.2% mortality in 2nd instar larvae was passed through a 100 K filter, the mortality dropped to 16.1%, and to 11.1% when passed through a 10 K filter. Oral injection of $4^{th}$ instar larvae with $3.2 \times 10^6$ bacteria resulted in 50% mortality in 96 hr. Control mortality, however, was 20%.

The invention is also directed to extracts obtained from the strain which have insecticidal activity. Extraction of toxin from the cells is accomplished using procedures known in the art. Exemplary procedures include: adding 0.1% detergent or 0.1% CHAPS buffer to a cell pellet in equal volume of the original culture; extraction is for 30 minutes with shaking at room temperature. Cells are removed by centrifugation; the supernatant contains the toxin. The entire extract without removal of the cells is also toxic. During our tests we used Triton X-100 as the detergent in order to carry out tests for toxicity as the Colorado Potato Beetle is sensitive to other detergents, however other detergents can be used to extract the toxin. We used a volume of detergent or buffer to a cell pellet in equal volume of the original culture for comparison of toxicity; however one could extract in a smaller volume and may concentrate the activity.

The present invention is further directed to methods of controlling insects using the unique bacterium of the invention. This aspect includes application of an effective insect control amount of the strain, application of an effective insect control amount of a supernatant, filtrate or extract containing an insecticidally active metabolite produced by the strain or application of combinations of the foregoing. The strain or supernatant or filtrate or extract is applied, alone or in combination, in an effective insect control or insecticidal amount. For the purposes of this invention, an effective amount is defined as that quantity of microorganism cells, supernatant, filtrate or extract, alone or in combination, that is sufficient to kill the target insect, increase mortality, or inhibit the incidence, growth, development or reproduction of the target insect. Typically, a concentration range about $4 \times 10^7$ to $2 \times 10^{10}$ colony forming units (CFU)/ml is effective. The effective rate can be affected by insect species present, stage of insect growth, insect population density, and environmental factors such as temperature, wind velocity, rain, time of day and seasonality. The amount that will be within an effective range in a particular instance can be determined by laboratory or field tests.

The strain and/or supernatants, filtrates or extracts encompassed herein are useful for controlling insects (organisms in the class Insecta), and find particular use for control of a variety of agronomically important insects. The strain and/or insecticidally active metabolites obtained from the strain are useful for control of insect pests. These include for example, leaf-feeding insects including insects of the order Coleoptera (beetles) such as *Chrysomelidae: Leptinotarsa decemlineata* (Say) (Colorado potato beetle) and *Diabrotica* spp. (corn rootworm), insects of the order Lepidoptera such as *Plutella xyostella* (Linnaeus) (diamondback moth) and sucking insects of the order Homoptera, in particular of the genus *Bemisia* such as *Bemisia argentifolii* Bellows & Perring (silverleaf whitefly). Other agriculturally important insects include, for example, Lepidoptera, Noctuidae: *Trichoplusia ni* (cabbage looper), *Pseudoplusia includens* (soybean looper), *Agrotis ipsilon* (black cutworm), *Caenurgina erechtea* (forage looper), *Helicoverpa zea* (corn earworm), *Heliothis virescens* (tobacco budworm), *Spodoptera frugiperda* (fall armyworm), *Spodoptera exigua* (beet armyworm), *Spodoptera ornithogalli* (yellowstriped armyworm), *Anagrapha falcifera* (celery looper), and *Pseudaletia unipuncta* (armyworm), *Anticarsia gemmatalis* (velvetbean caterpillar); Plutellidae: *Plutella xylostella* (diamondback moth); Pyralidae: *Achyra rantalis* (garden webworm), *Desmia funeralis* (grape leaffolder), *Diaphania hyalinata* (melonworm), and *Diaphania nitidalis* (pickleworm); Sphingidae: *Manduca quinquemaculata* (tomato hornworm), *Manduca sexta* (tobacco hornworm), *Eumorpha achemon* (achemon sphinx), *Agrius cingulata* (sweetpotato hornworm), and *Hyles lineata* (whitelined sphinx); moths such as gypsy moth (*Lymantria dispar*).

The invention also encompasses compositions which incorporate the strain of the invention and/or compositions comprising an insecticidally-active metabolite produced by the strain of the invention. Such compositions include, for example, whole broth cultures, liquid cultures, or suspensions of the strain; supernatants, filtrates or extracts obtained from the strain or combinations of the foregoing. Such insecticidally-active compositions may optionally include other ingredients such as an agricultural carrier, insect feeding stimulant, insect pheromone, insect attractant, fungicide, insecticide, photoactive dye, fluorescent brighteners, spreading agent, sticking agent, thickener, emulsifier, stabilizer, preservative, buffer, water, diluent or other additive as known in the art of formulation of insecticidal compositions. Insect feeding stimulants include, for example, cucurbitacins, e.g., cucurbitacin E-glycoside as described by Schroder et al. in U.S. Pat. Nos. 5,968,541 and 6,090,398. Photoactive dyes in combination with biological control agents are described by Martin et al., 1998. Fluorescent brighteners include, for example, those which provide protection for pathogens from the damaging effects of exposure to UV radiation and which may enhance biological activity of an organism as described by Shapiro et al. in U.S. Pat. No. 5,124,149. The bacterial biocontrol composition of the invention may also contain other insect biocontrol strains. The compositions are applied as known in the art to protect plants from insect pests. The compositions are applied in an area where a target insect is to be controlled, for example, application to soil in a field or surrounding a plant, to a target plant, e.g., to plant roots, on plant foliage, flowers, stems, seed, and tubers. The strain of the invention can be grown on rice grains and the rice grains applied to the plant or soil. Application of the compositions of the invention are carried out by any means known in the art, for example, spreading, spraying, drenching, drip irrigation of the insecticidal composition.

The invention also encompasses *Chromobacterium* strains which have a 16S rDNA gene sequence of SEQ ID NO:1. Such strains may be isolated for example using primers chromo 16SF1 (SEQ ID NO:2) and chromo 16SF2 (SEQ ID NO:3) and identified using SEQ ID NO:1.

EXAMPLES

The following examples are intended only to further illustrate the invention and are not intended to limit the scope of the invention which is defined by the claims.

Example 1

The following example describes the origin, isolation, culture conditions, and characterization of *Chromobacterium subtsugae* sp. nov.

Purple colonies of the bacterial strain of the invention were isolated from soil rich in hemlock leaves from a forest in western Maryland USA during a project looking for insect pathogens in nematodes. The pH of the soil was 4.7, and the moisture content was 46.6%. The original soil sample had a total aerobic microbial cell count of $1.75 \times 10^6$ cfu/g of soil, about half of which were purple colonies on RM (½L, Atlas, 1997). The colonies were plated on L-agar.

One purple colony was subsequently cultured on L. The strain was obtained in biologically pure form by dilution plating on L.

Further description of culturing of the strain of the invention: Bacteria were cultured in L-broth (Miller, 1972) or on L-agar. We also used RM medium (Martin et al., 1998), which contained half the nutrients of L, for bacterial recovery from insects.

Bacteria were grown on L-agar plates at 25° C. At preselected time intervals, bacteria were harvested from plates. Cells were titered and used directly or diluted in sterile water for insect bioassays.

For liquid cultures, cells were grown in L-broth or RM broth and shaken at 125 rpm for appropriate times at 25° C. Cells were titered and used directly or diluted in sterile water. Cell-free supernatants were obtained from liquid cultures that had been grown at 25° C. for 24 h shaking at 150 rpm, or from plates whose cells had been harvested in sterile water. Cells were removed by centrifugation and the resulting supernatant was sterilized by passage through a 0.45 µm nylon filter or a 0.45 µm PES filter (Millipore Corp., Bedford, Mass.).

For media studies: the strain was grown on a variety of peptone based media, TBAB (Difco, Sparks, Md.) with 5% sheep blood for hemolysis testing, *Bacillus cereus* selective agar (Oxoid Ltd., Basingstoke, England) with egg yolk for lecithinase and lipase testing, BUGM, for carbon oxidation and M-9 (Atlas, 1997) for growth on minimal media. Bacterial growth was monitored by measuring the $OD_{600}$ in liquid media. The effect of salinity at 25° C. was tested in L-broth, growth at various temperatures was determined by growth on L agar. The effect of pH on growth was determined in L-media adjusted to the appropriate pH with NaOH or HCl and measured at 3 d at 25° C. Substrate utilization was determined using Gram-Biolog microtiter plates (Biolog version 3.5, Hayward, Calif.) to measure oxidation of carbon sources.

For quantitative analysis of cellular fatty acid compositions, a loop of cell mass was harvested from TSA and fatty acid methyl esters were prepared and identified using procedures of the Microbial Identification System (MIDI). Fatty acid analysis was accomplished with the Sherlock Microbial Identification System (MIDI, Inc., Newark, Del.). Bacteria were grown and processed according to the standard MIDI method. Fatty acids were identified by gas chromatography using the FAST method. Bacteria were identified by comparing the fatty acid profiles to the TSBA40 database of organisms provided with the Sherlock software. The G+C content was determined by the method of Mesbah et al. (1989) using *E. coli* (ATCC 11775) as the method calibration. HPLC analyses were performed on an HP1100 using a Penomenex Luna C18(2) column (3 mm×250 mm). Calculations were based on the ratio of deoxyguanosine to thymidine. rDNA analysis was carried out as described in Example 2, below.

The purple bacteria were Gram negative rods and preliminarily identified as *C. violaceum* by comparison to descriptions in Bergey's manual (Sneath, 1984). When the first 500 bp of the 16S ribosomal DNA were sequenced the identification was to the genus *Chromobacterium* (Accugenix, Newark, Del.). Using Biolog, *Chromobacterium subtsugae* NRRL B-30655 was also identified as *C. violaceum*, but with a low similarity index (0.604), suggesting that the relationship to the type strain was not close. During the characterization of the toxic activity several important differences were noticed. The *C. violaceum* type strain, ATCC 12472, was not toxic to insects (data not shown). The type strain also grew at much high temperatures than NRRL B-30655. To confirm its identity we tried other methods of identification. For quantitative analysis of cellular fatty acid compositions, a loop of cell mass was harvested from TSA and fatty acid methyl esters were prepared and identified using procedures of the Microbial Identification System (MIDI). Fatty acid analysis was accomplished with the Sherlock Microbial Identification System (MIDI, Inc., Newark, Del.). Bacteria were grown and processed according to the standard MIDI method. The MIDI identified this strain as a *Pseudomonas coronafaciens* with a low similarity index (0.632) 16S rDNA confirmed that there were 23 differences from the closest named *Chromobacterium* species.

On the basis of 16S rDNA sequences, and other characteristics such as violacein production, lecithinase production, and casein hydrolysis, strain NRRL B-30655 is related to the genus *Chromobacterium*. The 16S rDNA sequencing indicated that *Chromobacterium subtsugae* NRRL B-30655, while belonging to the genus *Chromobacterium*, is different enough to be considered another species. However differences in 16S rDNA sequences, of lower temperature optimum, differences in fatty acid profile and insect toxicity suggest it is distinct from other described species in the genus. It has been proposed that members of the same genus should be regarded as separate species if they have less than 97% 16S rDNA similarity (Stackebrant & Goeble, 1994). On the basis of this criterion, as well as the phenotypic characteristics, we determined that strain NRRL B-30655 as a new species of the genus *Chromobacterium*, and designated the strain as *Chromobacterium subtsugae* sp. nov. This is described in detail in Example 2, below.

Strain NRRL B-30655 is a facultatively aerobic Gram-negative bacterium. Cells were tapered rods averaging 0.67±0.007 μm wide and 2.43±0.05 μm long. Occasionally cells were curved. Colonies were deep purple, smooth, regular and flat at 2–3 days. Colonies initially form at 24 h as small and cream colored and gradually turn light to dark purple from the center outward during the next 24 h. Colonies grew well on peptone based media as well as on the minimal medium, M-9, although on minimal media the colonies were a very faint purple. Colonies did not grow on rice extract agar. NRRL B-30655 grew optimally at 25° C., pH 6.5–8.0 and with 0–1.5% (w/v) NaCl. Growth was slow, but visible at 10° C. and at 40° C. Sparse growth occurs at 10–20° C. and 35–40° C. NRRL B-30655 does not grow on 3% NaCl. It grows from pH 5.0 to 9.0. It hydrolyzes casein and produces a lecithinase and lipase on egg yolk agar. It is not hemolytic on sheep blood. It produces purple pigment in the presence of oxygen which has the spectral and solubility properties of violacein. The amino acid utilization and fatty acid composition is as presented above. A complete 16S rDNA sequence of strain *Chromobacterium subtsugae* NRRL B-30655 was obtained and is shown in SEQ ID NO: 1. The G+C content of *Chromobacterium subtsugae* NRRL B-30655 was found to be 64.51% (s.d.=±0.14%).

Example 2

The following example describes the rDNA sequence of the strain of the invention and determination that the strain is a new species of the genus *Chromobacterium*, designated as *Chromobacterium subtsugae* sp. nov.

rDNA analysis was carried out as follows: For polymerase chain reaction (PCR) and sequencing, DNA was purified from strain *Chromobacterium subtsugae* NRRL B-30655 by standard methods (*Current Protocols in Molecular Biology*, Unit 2.4). 16S rDNA was amplified using primers universal to prokaryotes, R16F0 and R16R1 (Lee et al., 1993), and sequenced using Big Dye terminator chemistry on an ABI Prism Model 310 (PE Applied Biosystem, CA, USA) using these primers, and new primers chromol6SF1 (5'-AACGCTGGCGGCATGCTTTACAC-3') (SEQ ID NO:2) and chromol6SF2 (5'-GAGGAAATCCCGCTGGTTA-3) (SEQ ID NO:3) designed based on 16S rDNA sequence of *C. violaceum* (GenBank Accession M22510). The resulting strain *Chromobacterium subtsugae* NRRL B-30655 full 16S sequence is shown in SEQ ID NO:1. It has been deposited in GenBank under the Accession Number AY344056.

This and other *Chromobacterium* and representative members of the β-Proteobacteria 16S sequences were aligned separately by the CLUSTAL method, version V, with LaserGene software (DNASTAR, Inc. Madison, Wis., USA). Phylogenetic analyses were performed on a Power Macintosh G4 with the computer program PAUP (Phylogenetic Analysis Using Parsimony), version 4.0b5 (PPC), written by D. L. Swofford (Sinauer Associates). Uninformative characters were excluded from analysis and the phylogenetic tree was constructed by a heuristic search via random stepwise addition implementing the tree bisection and reconnection algorithm to find the optimal tree(s). *Escherichia coli* was designated as the out group to root the tree. The analysis was replicated 1000 times. Bootstrap analysis was performed to estimate stability and support for the inferred clades.

Phylogenetic analysis of 16S rDNA sequences revealed strain *Chromobacterium* subtsugae NRRL B-30655 and *Chromobacterium* species form a monophyletic clade, with closest ancestral taxon *Vogesella indigofera* (previously *Pseudomonas indigofera*, Grimes et al., 1997), within the β-Proteobacteria. The 16SrDNA sequence similarities between *Chromobacterium subtsugae* NRRL B-30655 and other clade members *C. violaceum* and *Chromobacterium* species MBIC3901 were high, 97.4% and 98.3%, respectively. The similarity between *Chromobacterium subtsugae* NRRL B-30655 and *V. indigofera*, the most closely related non-chromobacterium, was 90.7%.

On the basis of 16S rDNA similarity and phylogenetic analysis, *Chromobacterium subtsugae* NRRL B-30655 is clearly a member of the genus *Chromobacterium*. Stackebrant & Goeble (1994) proposed that members of the same genus should be regarded as separate species if they have less than 97% 16S r DNA similarity. However, they further noted that two organisms with 16S rDNA sequence homology below 97.5% are unlikely to have more than 60 to 70% DNA similarity, and thus they are related at the species level. Designating *Chromobacterium subtsugae* sp. nov. as a species separate from the genus type species *C. violaceum* and other chromobacteria is well supported. Differences in biological characteristics, such as temperature optimums and toxic activities suggest it is distinct from the other described species in the genus. Further, fatty acid analysis profiles indicate a potentially closer relationship to *V. indigofera*, the most closely related non-*Chromobacterium*, than to the *Chromobacterium* genus type species, suggesting that the new strain *Chromobacterium subtsugae* NRRL B-30655 is properly placed phylogenetically as the most basal strain within the *Chromobacterium* clade. On the basis of these polyphasic analyses, phylogenetic as well as phenotypic criteria, we propose strain *Chromobacterium subtsugae* NRRL B-30655 as a new species of the genus *Chromobacterium*, namely *Chromobacterium subtsugae* sp. nov. Other strains of this species can be isolated, for example, using primers chromo 16SF1 (SEQ ID NO:2) and chromo 16SF2 (SEQ ID NO:3) and identified using the full length 16S rDNA gene sequence (SEQ ID NO:1).

Example 3

The following example describe the further characterization of one or more insecticidally-active metabolites obtained from *Chromobacterium subtsugae* sp. nov.

To further characterize the one or more *Chromobacterium subtsugae* NRRL B-30655 toxins we filtered the aqueous supernatant through 100 K and 10 K polysulphone filters (VectaSpin 3, Whatman International Ltd., Maidstone, England) and evaluated their toxicity against $2^{nd}$ instar Colorado potato beetle. The filtered supernatant of *Chromobacterium subtsugae* NRRL B-30655 was exposed to heat (65° C. for 10 min) and protease XIV (Sigma, St. Louis, Mo.; 30° C. for 30 min) to test for toxin stability.

To obtain the one or more insecticidally active toxic agents, the strain of the invention is grown as described above. The one or more toxins are made after exponential growth ceases. For example, the strain normally grows at 25° C. and forms purple pigment in 48 hours when well aerated. This isolate is unlike the type strain of *C. violaceum* (ATCC 12472) as it does not grow above 35° C. While insect toxin formation is heat sensitive, we found that the toxin itself, after formation, is stable when: frozen, heated to 65° C. for 10 min, stored at room temperature for 28 d, and exposed to either acid (pH 2) or base (pH 9). Heat treatment at 90° C. for 10 minutes generally reduced toxicity, but the extent of reduction depended on the age of the culture. Most of the one or more insecticidally active metabolites were retained by a 100 K filter. Some activity remained after passage through a 10 K filter. The one or more active toxins were not recovered after filtering though a 100 Mdalton filter. These data suggested a large and stable macromolecule. The bacterial strain may be producing multiple toxins with varying properties, as treatment with protease or heat seems to affect some of the toxicity, but not all. Treatment of fresh cultures with an exo-protease also reduced toxicity, suggesting that the one or more toxins may be a protein. It appears that the one or more toxins are cell associated and are released from or are less associated with the cells as the culture ages, or by extraction with detergents or buffers that are known to release molecules from membranes. They do not appear to be typical proteins based on their heat and acid stability. The uniqueness of the one or more toxic agents is indicated by the properties of heat stability and protease resistance.

Toxin production was genetically stable over time. In 20 transfers in liquid culture, the $19^{th}$ transfer was as toxic as the initial culture, though the toxicity varied among transfers depending on the time of harvest. While most cultures formed the purple pigment that is indicative of *Chromobacterium*, some did not. Pigment formation was not an indicator of toxicity. The non-pigmented cultures gave rise to pigmented cultures and colonies formed when titering the liquid cultures were always purple. In a parallel experiment with a liquid medium with reduced nutrients, at the 11th transfer, some non-pigmented colonies appeared on the titer plates. Most of these colonies upon subculture quickly reverted to pigmented types. However, one mutant remained non-pigmented. Its relation to the parental strain was confirmed by fatty acid analysis of the membrane, but not by ribotyping. This mutant was no longer toxic to Colorado potato beetle larvae. This non toxic mutant is useful to characterize the one or more toxins produced by strain NRRL B-30655.

Example 4

The following example describes insect bioassays which demonstrate the toxicity of *Chromobacterium subtsugae* sp. nov. and toxins produced by *Chromobacterium subtsugae* sp. nov. tested against the Colorado potato beetle.

*Bacillus thuringiensis* var. *tenebrionsis* NTEN3-2 was obtained from Novodor FC (Abbott Labs, Chicago, Ill.) and used for comparisons of toxicity.

Insects. The Colorado potato beetle colony, in the USDA, ARS, Insect Biocontrol Laboratory, Beltsville, Md., originated from eggs sent from the New Jersey Department of Agriculture in 1996. The colony has been maintained on potato foliage. Field-collected insects from Beltsville, Md. are introduced yearly to maintain genetic diversity. Colorado potato beetle adults were fed potato foliage and eggs laid on potato foliage were harvested, hatched, and placed on diet. Insects were reared from eggs for bioassays on IBL potato leaf diet in 100 mm×20 mm Petri dishes in paper bags. The IBL diet was a modification of the Forester diet (Gelman et al., 2001) made with defined ingredients as well as potato leaf powder, tomato fruit powder and neomycin. Per liter batch the ingredients are: 60 g torula yeast (ICN, Biomedicals, Aurora, Ohio), 40 g rolled oats (Quaker Old Fashioned), 30 g lactoalbumin hydrolysate (Bioserve, Frenchtown, N.Y.), 10 g casein (Bioserve, Frenchtown, N.Y.), 25 g potato leaf powder (Superior), 12.5 g tomato fruit powder (cv. "Better Boy"), 20 g fructose (USB, Cleveland, Ohio), 12 g Roche vitamin mix (Bioserve, Frenchtown, N.Y.) 4 g Beck's salt mix (Bioserve, Frenchtown, N.Y.) 1 g beta sitosterol (USB, Cleveland, Ohio), 0.8 g methyl paraben (USB, Cleveland, Ohio), 0.8 g sorbic acid (Bioserve, Frenchtown, N.Y.), 0.2 g neomycin sulfate (ICN, Biomedicals, Aurora, Ohio), 2 ml wheat germ oil (ICN, Biomedicals, Aurora, Ohio), 2 ml soybean oil (Wesson), 14 g agar (Bioserve, Frenchtown, N.Y.), and 768 ml distilled water. Incubation was initially in the dark so that the larvae would feed on the diet, and then on a light-dark regime of 16:8 (L:D) with 46% relative humidity (RH) at 24° C. Diet was changed every 4 days.

Freeze-dried diet. For bioassays the diet was used as re-hydrated freeze-dried pellets. The standard diet was made as described without neomycin. It was poured into 96-well polypropylene plates (GreinerBioOne, Longwood, Fla.), frozen overnight (−20° C.), and dried in a Virtis Advantage Freeze Drier (The Virtis Co., Inc., Gardiner, N.Y.) under the following conditions. Frozen diet in 96-well plates was placed on shelves that were frozen to −45° C. and held for 20 min. The diet was dried in nine steps under vacuum at 15 mTorr: −40° C. for 600 min, −30° C. for 420 min, −20° C. for 300 min, −10° C. for 300 min, 0° C. for 60 min, 10° C. for 60 min, 20° C. for 120 min, 30° C. for 120 min and 40° C. for 120 min. The first four steps are the primary drying phase and the last six steps are needed for secondary drying. Without secondary drying, the pellets tended to be spongy and did not absorb liquid well. After releasing the vacuum, the 96-well plates were removed from shelves, dried diet pellets were removed from the 96-well plates, placed in sterile plastic bags, and stored at 4° C. before use. The dried diet pellets, which had lost 0.302±0.011 g/pellet (mean±SEM), were stored in sterile plastic bags at 4° C. until used.

For each treatment in a bioassay 32 diet pellets were used. For freeze-dried diets, pellets were either re-hydrated with 0.3 ml, determined from the loss in weight from the fresh pellets, of water (controls) or suspensions containing dilutions of the pathogen (treatments). One $2^{nd}$ instar Colorado potato beetle larva was added to each diet pellet. Trays containing pellets were covered with bioassay tray covers (C-D International, Ocean City, N.J.). Holes were made in the covers with insect pins. Insects were incubated as described for rearing and mortality was recorded at 24, 48, 72, 96, and 120 h. Cell counts were used because the specific mode of action is not yet known for all pathogens, and cell counts could be used to compare pathogens with unknown modes of action. Assays with control mortality above 5% were discarded.

Statistical analysis. $LT_{50}$s were also calculated from the PROBIT procedure (SAS Institute, 1999) for the hour at which the mortality was recorded with 95% confidence intervals. Differences in weights were analyzed using MIXED procedure and means were separated using least significant difference, $\alpha=0.05$ and a macro (Saxton, 1998).

In 10 separate bioassays performed over the course of 2 years on the standard diet without neomycin, the variability in mortality for a concentration approximating the $LC_{50}$ at 96 h for *Chromobacterium subtsugae* NRRL B-30655 ranged from 37.4–63.9% (Table 1). Freeze-dried diets for Colorado potato beetle have been used in more than 130 bioassays over the same two year period. The age of the diets ranged from 1 day to more than 3 months. Although there were differences in the control mortality, total pathogen mortality, or $LT_{50}$ based on the age of the diet, the trends were minor and could be opposite for different batches of diet (Table 1).

TABLE 1

Variability of mortality of $2^{nd}$ instar Colorado potato beetle fed a single dose of *Chromobacterium suttsuga* NRRL V-30655 approximating an $LC_{50}$ at 96 h

| Batch No. | Age of Diet (d) | % Mortality | $LT_{50}$ in h (95% CL) |
|---|---|---|---|
| 1 | 8 | 39.4 | 110.3 (92.0–162.6) |
| 1 | 106 | 46.9 | 98.1 (88.1–117.9) |
| 2 | 31 | 37.5 | 105.5 (92.5–137.2) |
| 2 | 45 | 37.5 | 107.5 (89.8–159.4) |
| 2 | 69 | 60.0 | 88.1 (76.4–109.8) |
| 2 | 83 | 63.6 | 82.7 (72.4–99.0) |
| 3 | 1 | 48.9 | 93.0 (83.3–110.2) |
| 4 | 24 | 53.1 | 91.8 (77.1–125.5) |
| 4 | 35 | 42.9 | 97.2 (88.8–113.2) |
| 4 | 55 | 37.6 | 102.3 (89.9–130.8) |
| Mean | | 46.7 | 99.8 (92.6–110.0) |

To fulfill Koch's postulates, $2^{nd}$ instar larvae that had died after treatment with bacteria were surface sterilized, placed in a 1.5 ml micro centrifuge tube, 0.5 ml water was added, and the cadaver ground with a motorized pestle (Sigma, St. Louis, Mo.). Insect parts were allowed to settle and dilutions were plated and incubated at 25° C. for 48 h in order for pigmented microbes to be distinguished. Substrate utilization profiles of the recovered microbes were compared to the microbes originally fed using Biolog system of identification (version 3.5).

While $1^{st}$ instar Colorado potato beetle larvae were most susceptible to the bacterium of the invention, it is just not practical for field applications to test against $1^{st}$ instar larvae as this larval stage is the shortest and causes the least damage. The time to kill $2^{nd}$ instar larvae can be somewhat variable depending on whether the larvae were starved or fed, but at high doses usually all larvae are dead by 120 h. The decrease in the $LC_{50}$ from $2^{nd}$ to $3^{rd}$ instar larvae for *Chromobacterium subtsugae* NRRL B-30655 is not due to increased sensitivity to toxin, but to increased consumption of the toxin.

Figure 1:
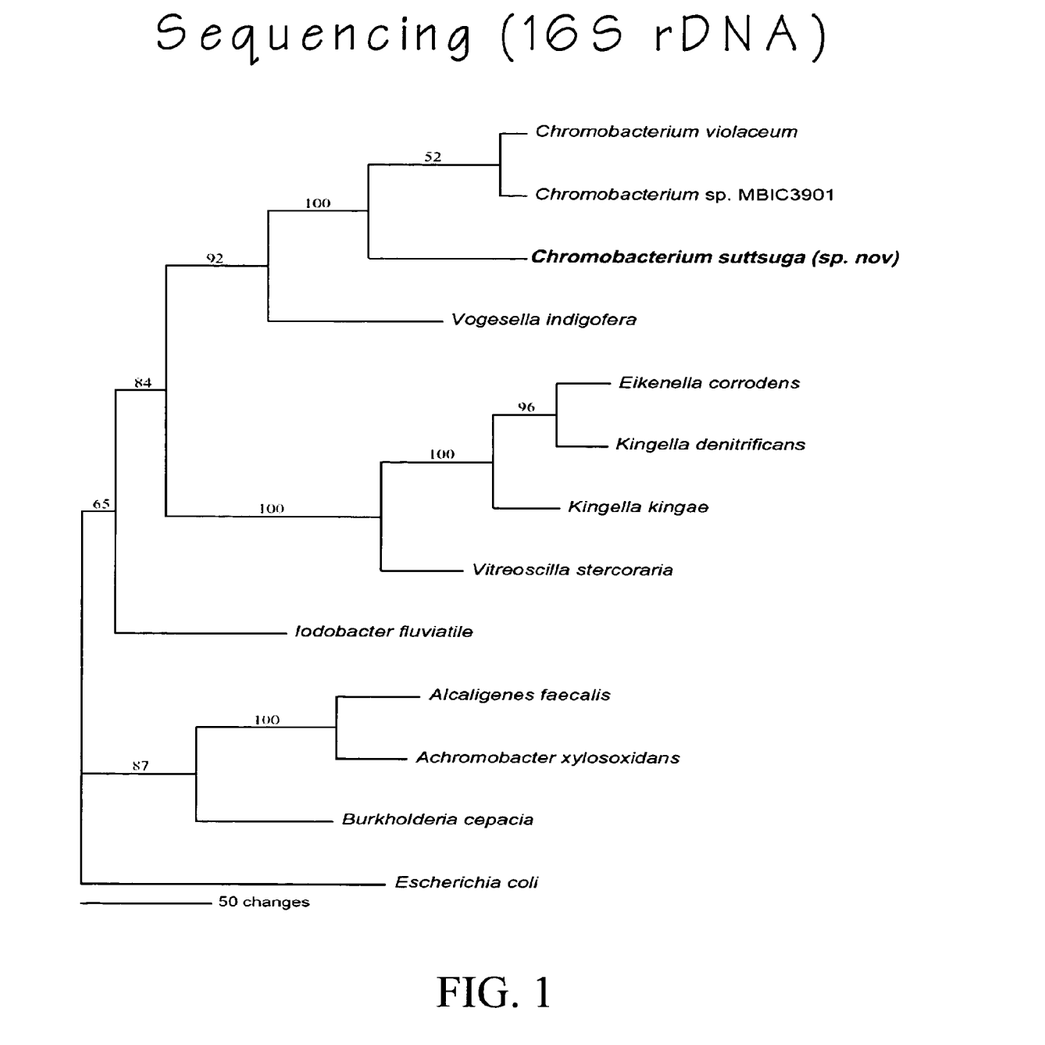
Figure 2:
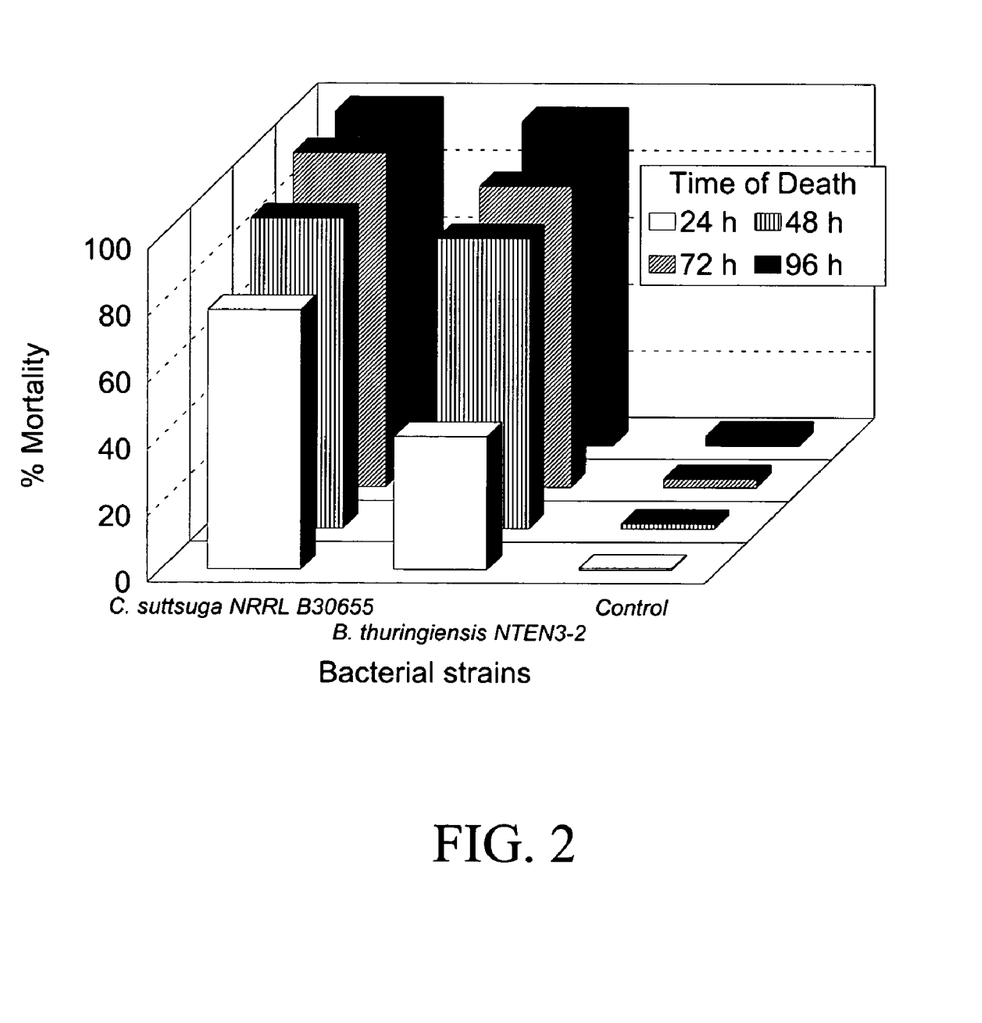

Results: Insect Bioassays. In an initial comparison of strains, it was found that the toxicity of *Chromobacterium subtsugae* NRRL B-30655 was similar to *B. thuringiensis* NTEN3-2 toxicity fed to $2^{nd}$ instar Colorado potato beetle larvae at the same dilution (FIG. 2) This comparison was made when the bacteria were grown on the same media under identical conditions with stationary phase (48 hour) cultures. In this preliminary experiment, both *P. luminescens* HM5-1 and *Chromobacterium subtsugae* NRRL B-30655 killed the larvae faster than the *B. thuringiensis* NTEN3-2.

In the first bioassay, over 78% of the $2^{nd}$ instar beetle larvae died within 3 days. The larvae also appeared to stop feeding, no diet was consumed and little to no frass was produced even by the survivors.

*Chromobacterium subtsugae* NRRL B-30655 purple pigmented colonies were recovered from 12 of 30 insects that died after exposure to *Chromobacterium subtsugae* NRRL B-30655 whole cultures. The total number of bacteria recovered per larvae averaged $1.15\pm0.95\times10^7$, while the amount of *Chromobacterium subtsugae* NRRL B-30655 recovered ranged from $2.5\times10^3$ from a larvae that died at 24 h to a high of $6.5\times10^5$ from a larvae that died at 72 h. Purple bacteria grown from colonies recovered from these insects were also toxic to Colorado potato beetle larvae when fed to larvae ($2.5 \times 10^8$ cfu/diet pellet) after growth on L-agar for 48 h.

Figure 3:
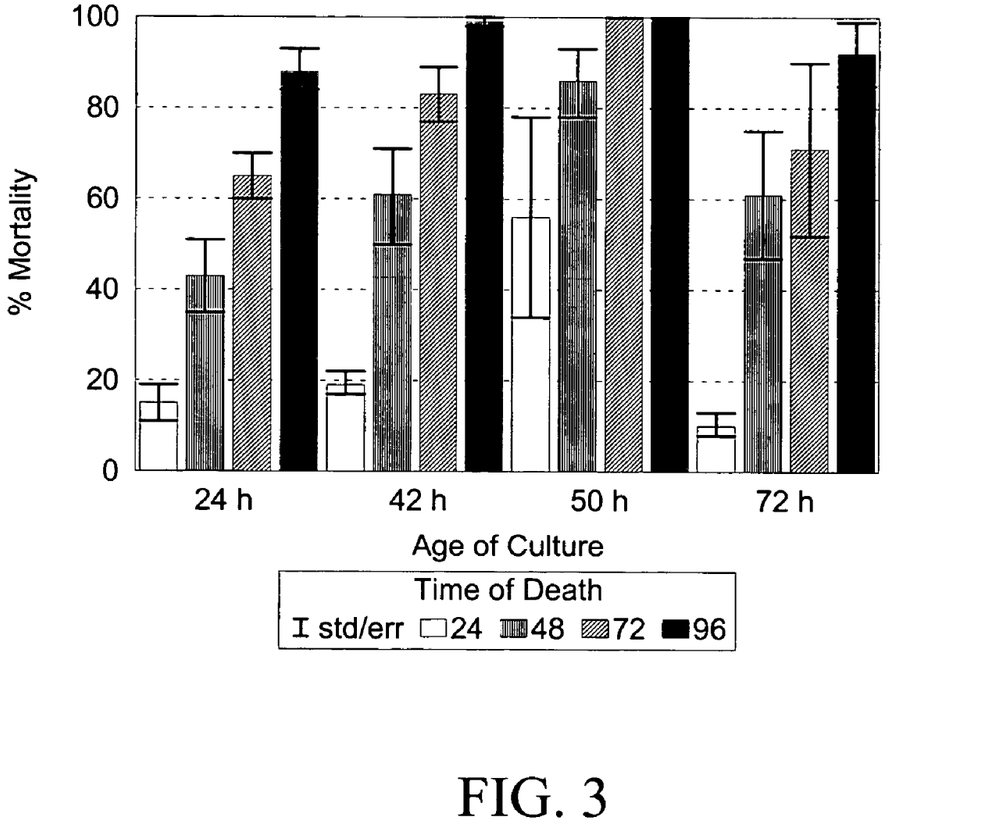

The age of the *Chromobacterium subtsugae* NRRL B-30655 made more of a difference in initial mortality, but not total mortality (FIG. 3). At 25° C. the doubling time was 40 minutes and stationary phase was reached within 24 hours. The toxic activity of *Chromobacterium subtsugae* NRRL B-30655 appeared later with maximum toxicity of cultures grown on solid media occurring at 52 h (100% mortality at 72 h). As *Chromobacterium subtsugae* NRRL B-30655 cultures aged to 10 d, the titer dropped to less than 1,000 viable cells, but the toxicity remained high (84% mortality), even though larvae did not start to die until 48 h after being placed on the diet (data not shown). Further stability studies conducted on a 28 d liquid whole culture had 87.4% mortality.

In liquid culture, *Chromobacterium subtsugae* NRRL B-30655 had high toxicity (75% mortality) incubated at 25° C., 125 rpm for 24 h. The toxicity in liquid culture grown for 24 h decreased (25% mortality) with increased shaking speed (150 rpm) and increased temperature (27° C.). In one experiment, when the culture temperature was inadvertently raised during growth to 35° C. no measurable toxicity was noted in the bioassay and no viable cells were recovered.

First instar larvae were the most susceptible to *Chromobacterium subtsugae* NRRL B-30655. Starving the larvae before placing them on the diet did not change the total mortality, but did affect how quickly they died. In an experiment comparing fed and starved late $1^{st}$ instar larvae, 81.3% of the starved larvae died within 24 h after being exposed to pellets to which $7.2\times10^8$ *Chromobacterium subtsugae* NRRL B-30655 cells had been added. Only 56.3% of the fed larvae were dead at 24 h after exposure to the same dose. Second instar fed larvae exposed to the same dose, at the same time showed 91% survival at 24 h. The $LC_{50}$ for *Chromobacterium subtsugae* NRRL B-30655 unexpectedly decreased from $2^{nd}$ to $3^{rd}$ instar larvae (Table 2).

TABLE 2

$LC_{50}$ of Colorado potato beetle by instar after 96 hr

| Stage | *Chromobacterium suttsuga* NRRL B-30655 |
|---|---|
| $1^{st}$ instar | $8.0 \times 10^6$ |
| $2^{nd}$ instar | $2.0 \pm 0.79 \times 10^8$ |
| $3^{rd}$ instar | $3.24 \pm 1.18 \times 10^7$ |
| Adult | none[b] |

[a]mean ± standard error of bacteria applied per pellet based at least 3 bioassays with 5 concentrations per bioassay and $LC_{50}$ calculated by PROBIT analysis. First instar assay was not replicated.
[b]Adult beetles stopped eating.

When filter-sterilized supernatants of *Chromobacterium subtsugae* NRRL B-30655 were tested against $2^{nd}$ instar Colorado potato beetle larvae, the toxicity was dependent on the age of the culture. Cell free supernatants from cultures up to 48 h old had only 9–20% the toxicity of the whole culture (Table 3), while the toxicity of supernatants from cultures older than 72 h was 55–86% of whole cultures (Table 3). This confirmed previous observations that cultures older than 7 days with few viable cell counts were also toxic, however peak toxicity occurred when cell number was maximal. Filtered supernatants were clear or only slightly purple compared to whole cultures when filtered through nylon filters. Supernatants filtered through PES membranes retained their purple color.

For *Chromobacterium subtsugae* NRRL B-30655, there were no differences in toxicity of filtrates that were heated to 65° C. for 10 min (60% filtrate, 61.5% heat-treated filtrate). There was a slight decrease in toxicity when filtrates were treated with protease type XIV (51.7% protease-treated filtrate) compared to those filtrates that were not treated. When a supernatant that caused 55.2% mortality in $2^{nd}$ instar larvae was passed through a 100 K filter, the mortality dropped to 16.1%, and to 11.1% when passed through a 10 K filter.

Oral injection of $4^{th}$ instar larvae with $3.2\times10^6$ bacteria resulted in 50% mortality in 96 hr. Control mortality, however, was 20%.

TABLE 3

Comparison of mortality of whole cultures and sterile supernatants of NRRL B-30655

| Culture type | % Mortality 24 h | 48 h | 72 h | 96 h |
|---|---|---|---|---|
| 48 h whole culture[a] | 15.2 | 36.4 | 63.6 | 84.3 |
| 48 h filtered supernatant | 3.0 | 9.1 | 9.1 | 15.6 |
| 96 h whole culture[b] | 0 | 28.1 | 53.1 | 100 |
| 96 h filtered supernatant | 0 | 13.3 | 60.0 | 86.0 |

[a]$8.15 \times 10^8$ viable cells applied per pellet
[b]fewer than 10,000 viable cells applied per pellet In sum, the $LC_{50}$ for *Chromobacterium subtsugae* NRRL B-30655 to 2nd instar Colorado potato beetle larvae was $2.0\pm0.8\times10^8$ cells per diet pellet. For first instar larvae, the $LC_{50}$ was approximately $8\times10^6$ cells per diet pellet and for third instar larvae the $LC_{50}$ was approximately $3\times10^7$ cells per diet pellet. The first indication of toxicity was the larvae stopped feeding. Although bacteria were applied at a high concentration to each pellet it was apparent that the larvae consumed very little diet which would indicate a much lower lethal dose than the concentration applied to the diet pellet. The most noticeable observation compared to the control was the lack of frass production, implying that the *Chromobacterium subtsugae* NRRL B-30655 cultures had anti-feeding activity. Alternatively, the toxic factor(s) may act on the insect midgut; decreased frass production is a commonly observed symptom of toxins which destroy the midgut, such as the δ-endotoxins of *B. thuringiensis* or the Tc proteins of *P. luminescens*.

Example 5

The following example describes insect bioassays which demonstrate the toxicity of *Chromobacterium subtsugae* sp. nov. tested against the corn rootworm, diamond back moth, gypsy moth, and *Culex pipiens* (mosquito).

Corn Rootworm Bioassays and Results. Corn root worm assays were performed with field collected adult beetles of mixed sexes. Because we had a feeding stimulant for adult corn rootworm, we tested the bacteria against the adults. NRRL B-30655 was mixed with a cucurbitacin based feeding stimulant, and a starch and applied in 50 μl aliquots to 100 mm petri dishes (Schroder et al. 2001). Five beetles were added to each dish and controls (without the bacteria) and treatments were repeated five times. Mortality was recorded at 5 days after treatment. Eighty percent of the western or southern corn rootworm adult beetles which fed on the combination of feeding stimulant and NRRL B-30655 died within 5 days.

Other Insect Bioassays. To determine if other orders of insects could be affected, we chose the diamondback moth and gypsy moth as Lepidoptera to test. Diamond back moth (*Plutella xylostella*) larval assays were done on leaf disks (Farrar et al. 2001). Gyspy moth (*Lymantria dispar*) assays were the same as Colorado potato beetle only with using gypsy moth diet (Bell et al. 1981). Gypsy moth larvae were weighed at 7 d to determine sublethal effects. Gypsy moth egg masses were obtained from APHIS Otis Air Force Base and reared to $2^{nd}$ instar on the same diet. *Bacillus thuringiensis* NRRL strain B-18195 was included as a positive control. In addition, mosquitoes from the order Diptera were also tested. *Culex pipiens* egg rafts were collected locally and mosquito larvae were raised in white enamel pans with two inches deionized water and fed fish chow. Ten $3^{rd}$ instar larvae were tested in 10 ml deionized water in scintillation vials to which 100 µl of a *Chromobacterium subtsugae* NRRL B-30655 culture was added. Mortality was recorded at 24 and 48 h. *B. thuringiensis* var. *israelensis* IPS 89 was used as a positive control.

Results. For diamondback moth $2^{nd}$ instar larvae the mortality was 90% in 7 d. None of the gypsy moth larvae died following treatment with NRRL B-30655, but the larvae which consumed NRRL B-30655 in their diet were 40% lighter than the controls. For mosquito larvae, there was no mortality at 48 h although the larvae in the *B. thuringiensis* control were dead in 16 h.

Example 6

The following example describes the strain of the invention in combination with another pathogen for control of insect pests.

*Chromobacterium subtsugae* NRRL B-30655 in combination with *S. marcescens* TERM was fed to Colorado potato beetle larvae. The toxicity of the combination was additive. Using the chi square test, the sum of the two individual toxicities was not different than the two in combination (df=3, $\chi^2$=1.54, P=0.68). This combination was repeated three times with different concentrations of the strains with similar results. The results are shown in the Table 4, below.

TABLE 4

Mortality of $2^{nd}$ instar Colorado potato beetle fed artificial diet containing combinations of bacteria.

| | % Mortality | | | |
|---|---|---|---|---|
| Strains | 24 h | 48 h | 72 h | 96 h |
| C. suttsuga NRRL B-30655 | 3.2 | 21.9 | 25.0 | 34.3 |
| S. marcescens TERM | 3.2 | 12.5 | 15.6 | 28.1 |
| B-30655 + TERM | 18.8 | 37.5 | 40.6 | 59.4 |

Example 7

The following example describes the effects of *Chromobacterium subtsugae* NRRL B-30655 in combination with an optical brightener on Colorado potato beetle larvae.

*Chromobacterium subtsugae* NRRL B-30655 in combination with an optical brighter was tested for activity against the Colorado potato beetle. The optical brightener, Tinopal LPW, was chosen to test at molar concentrations near the 1% and 0.1% concentrations used for viral enhancement in Lepidoptera.

Results. For *Chromobacterium subtsugae* NRRL B-30655-treated Colorado potato beetle larvae, the mortality increased from 62.8 to 87.9% ($\chi^2$=63.04 df=4 P<0.01, titer=2.4×$10^8$ cells/pellet; Table 5) with the addition of Tinopal LPW. Mortality of 80–90% was also obtained with a 1:2 dilution of *Chromobacterium subtsugae* NRRL B-30655. The larvae exposed to the *Chromobacterium subtsugae* NRRL B-30655+Tinopal LPW combination began dying 24 h earlier (Table 6). When weighed at 6 d, the control larvae were heavier (13.1±1.1 mg) than the optical brightener treated larvae (10.6±1.1 mg). The weights of the surviving larvae treated with *Chromobacterium subtsugae* NRRL B-30655 (3.1±0.5 mg) or *Chromobacterium subtsugae* NRRL B-30655+Tinopal LPW (4.4±0.6 mg) were less than half the control weights. In replicated experiments the increase in mortality was similar (65.6% to 81.55%, titer=5.3×$10^8$ cells/pellet) but the larvae always died earlier.

Because no *Chromobacterium subtsugae* NRRL B-30655 cells are recoverable from cultures greater than 10 d old, (titer <30 cells/diet pellet), these suspensions must kill by toxin. The toxin suspensions were also tested in combination with Tinopal LPW at 1 mM. At 72 h after being exposed to a 1:10 dilution of a 10 d *Chromobacterium subtsugae* NRRL B-30655 culture scraped from a plate, the larval mortality increased from 56% to 94% ($\chi^2$=11.13, df=4, P=0.033). The $LT_{50}$ for the *Chromobacterium* NRRL B-30655 10 d culture alone was 75.6 h (95% CL: 68.9–82.4), whereas the $LT_{50}$ for the *Chromobacterium subtsugae* NRRL B-30655 10 d culture+Tinopal LPW combination was 48.6 h (95% CL: 43.4–53.8). In this case only a toxin was involved as no viable cells were recovered.

We also tested the toxin of *Chromobacterium subtsugae* NRRL B-30655 with a lower concentration of Tinopal LPW (0.5 mM) and at this concentration larval mortality increased, but not significantly, from 68.8% to 75% ($\chi2$=2.11, df=4, P=0.674). However, the $LT_{50}$ (while longer than the previous experiment for *Chromobacterium* subtsugae NRRL B-30655 alone (85.0 h, 95% CL: 78.0–92.4)) still decreased by almost 10 h (75.6 h, 95% CL 67.7–83.5) for the *Chromobacterium subtsugae* NRRL B-30655/Tinopal LPW combination.

TABLE 5

Mortality of Colorado potato beetle larvae with and without optical brightener

| | | % Mortality | | |
|---|---|---|---|---|
| Pathogen | Time | Optical brightener | Pathogen alone | Pathogen + optical brightener |
| Chromobacterium suttsuga NRRL B-30655[a] | 24 h | 0 | 0 | 0 |
| | 48 h | 3.1 | 0 | 21.2 |
| | 72 h | 3.1 | 25.7 | 54.5 |
| | 96 h | 6.3 | 42.9 | 72.7 |
| | 120 h | 6.3 | 62.8 | 87.9 |

[a]used at a concentration near the $LC_{50}$ 48 h culture

TABLE 6

| Effect of optical brightener on the speed of kill of Colorado potato beetle larvae by bacterial pathogens | | |
|---|---|---|
| | $LT_{50}$ (95% CL)* | |
| Pathogen | Pathogen alone | Pathogen + optical brightener |
| *Chromobacterium suttsuga* NRRL B-30655[a] Results of a typical experiment. | 104.2 (96.2–115.0) | 76.1 (68.6–83.7) |

[a]used at a concentration near the $LC_{50}$ 48 h culture
*$LT_{50}$ expressed in hours.

It is understood that the foregoing detailed description is given merely by way of illustration and that modification and variations may be made within, without departing from the spirit and scope of the invention. All publications, patents, and sequence listings cited herein are hereby incorporated by reference in their entirety.

REFERENCES

Atlas, R. M. (1997) *Handbook of Microbiological Media*. p. 726. Boca Raton: CRC Press, Inc.

Bell, R. A., Owens, C. D., Shapiro, M. & Tardif, J. G. R. (1981). Development of mass rearing technology, pp. 599–633. In *The gypsy moth: research toward integrated pest management*. C. C. Doane and M. L. McManus eds) *U.S. Department of Agriculture Technical Bulletin* 1584.

Blackburn, M., Golubeva, E., Bowen, D. and ffrench-Constant, R. H. 1998. A novel insecticide from *Photorhabdus luminescens*, toxin complex a (Tca) and its histopathological effects on the midgut of *Manduca sexta. Appl. Environ. Microbiol.* 64, 3036–3041.

Bowen, D. J. and Ensign, J. C. 1998. Purification and characterization of a high-molecular-weight insecticidal protein complex produced by the entomopathogenic bacterium *Photorhabdus luminescens. Appl. Environ. Microbiol.* 64, 3029–3035.

Bowen, D., Rocheleau, T. A., Blackburn, M., Andreev, O., Golubeva, E., Bhartia, R. and ffrench-Constant, R. H. 1998. Insecticidal toxins from the bacterium *Photorhabdus luminescens. Science.* 280, 2129–2132.

Bucher, G. E. 1981. Identification of bacteria found in insects. In "Microbial Control of Pests and Plant Diseases 1970–1980", (H. D. Burges, Ed.), pp. 7–33. Academic Press, New York.

Buyer, J. S. (2002). Rapid sample processing and fast gas chromatography for identification of bacteria by fatty acid analysis. *J. Microbiol Methods.* 51,209–215.

Dutky, S. R. 1940. Two new spore-forming bacteria causing milky diseases of Japanese beetle larvae. *J. Agr. Research.* 61, 57–68.

Duran, N., Erazo, S. and Campos, V. 1983. Bacterial chemistry II. Antimicrobial photoproduct from pigment of *Chromobacterium violaceum. Anais da Academia Brasileira de Ciéncias.* 55, 231–234.

Duran, N., Antonio, R. V., Haun, M. and Pilli, R. A. 1994. Biosynthesis of a trypanocide by *Chromobacterium violaceum. World J. Microbiol. Biotechnol.* 10, 685–690.

Farrar, R. R., Martin, P. A. W. & Ridgway, R. L. (2001). A strain of *Serratia marcescens* (Enterobacteriaceae) with high virulence per os to larvae of a laboratory colony of the corn earworm (Lepidoptera: Noctuidae). *J Entomol Sci.* 36, 380–390.

Ferro, D. N., Slocombe, A. C. and Mercier, C. T. 1997. Colorado potato beetle (Coleoptera: *Chrysomelidae*): residual mortality and artificial weathering of formulated *Bacillus thuringiensis* subsp. *tenebrionis. J. Econ. Entomol.* 90, 574–582.

Forst, S. and Nealson, K. 1996. Molecular biology of symbiotic pathogenic bacteria *Xenorhabdus* spp. and *Photorhabdus* spp. Microbiol. Rev. 60, 21–43.

Gelman, D. B., Bell, R. A., Liska, L. J., and Hu, J. S. 2001. Artificial diets for rearing Colorado potato beetle, *Leptinotarsa decemlineata. J. Insect Science.* Vol. 1, No. 7, pp1–11.

Grimes, D. J., Woese, C. R., MacDonell, M. T., Colwell, R. R. 1997. Systematic study of the genus *Vogesella* gen. nov. and its type species, *Vogesella indigofera* comb. nov. *Int JSyst Bacteriol.* 47,19–27.

Groden, E., and Lockwood, J. L. 1991. Effects of soil fungistasis on *Beauveria bassiana* and its relationship to disease incidence in the Colorado potato beetle *Leptinotarsa decemlineata*, in Michigan and Rhode Island. *J. Invertebr. Pathol.* 57, 7–16.

Guo, L., Fatig, R. O. III, Orr, G. L., Schafer, B. W., Strickland, J. A., Sukhapinda, K., Woodsworth, A. T., and Petell, J. T. 1999. *Photorhabdus luminescens* W-14 insecticidal activity consists of at least two similar but distinct proteins: purification and characterization of toxin A and toxin B. *J. Biol. Chem.* 274, 9836–9842.

Hackett, K. J., Whitcomb, R. E., Clark, T. B., Henegar, R. B., Lynn, D. E., Wagner, A. G. Tully, J. G., Gasparich, G. E., Rose, D. L., and Carle, P. 1996. *Spiroplasma leptinotarsae* sp. nov., a mollicute uniquely adapted to its host, the Colorado potato beetle, *Leptinotarsa decemlineata* (Coleoptera: *Chrysomelidae*). *Int. J. Syst. Bacteriol.* 46, 906–911.

Jackson, T. A., Huger, A. M. and Glare, T. R. 1993. Pathology of amber disease in the New Zealand grass grub, *Costelytra zealandica* (Coleoptera: *Scarabaidae*). *J. Invertebr. Pathol.* 61, 123–130.

Lee, I. M., Hammond, R. W., Davis, R. E., and Gundersen, D. E. 1993. Universal amplification and analysis of pathogen 16S rDNA for classification and identification of mycoplasmalike organisms. *Mol. Plant Pathol.* 83, 834–842.

Martin, P. A. W., Mischke, S. and Schroder, R. F. W. 1998. Compatibility of photoactive dyes with insect biocontrol agents. *Biocontrol Science Technol.* 8, 501–508.

Martin, P. A. W. and Schmidtmann, E. T. 1998. Isolation of aerobic microbes from *Ixodes scapularis* (Acari: *Ixodidae*), the vector of Lyme disease in the eastern United States. *J. Econ. Entomol.* 91, 864–868.

Martin, P. A. W., Schroder, R. F. W., Poprawski, T. J., Lipa, J. J., Hausvater, E. and Rasocha, V. 1999. Temperature effects on the susceptibility of the Colorado potato beetle (Coleoptera: *Chrysomelidae*) to *Beauveria bassiana* (*Balsamo*) Vuillemin in Poland, Czech Republic and the United States. *J. Entomol. Science.* 35, 251–258.

Mesbah M., Premachandran U. & Whitman W. B. (1989). Precise measurement of the G+C content of deoxyribonucleic acid by high-performance liquid chromatography. *Int J Syst Bacteriol.* 39, 159–67.

MIDI, Inc. (2002). Sherlock Microbial Identification System Version 4.5. MIS Operating Manual July. MIDI, Inc., Newark, Del.

Miller, J. H. 1972. "Experiments in Molecular Genetics". Cold Spring Harbor Laboratory Press, Cold Spring Harbor.

Ohba, M., Iwahana, H., Asano, S., Suzuki, N., Sato, R. and Hori, H. 1992. A unique isolate of *Bacillus thuringiensis* serovar *japanensis* with a high larvicidal activity for scarabaeid beetles. *Lett. Appl. Microbiol.* 14, 54–57.

Onstad, D. W. EDWIP: Ecological Database of the World's Insect Pathogens. Champaign, Ill.: Illinois Natural History Survey, [15/10/2001]. http://insectweb.inhs.uiuc.edu/Pathogens/EDWIP/index.html Perlak, F. J., Stone, T. B., Muskopf, Y. M., Peterson, L. J., Parker, G. B., McPherson, S. A., Wyman, J., Love, S., Reed, G., Biever, D., and Fishchoff, D. A. 1993. Genetically improved potatoes: protection from damage by Colorado potato beetle. *Plant Mol. Biol.* 22, 313–321.

Poprawski, T. J., Carruthers, R. I., Speese III, J., Vacek, D. C., and Wendel, D. E. 1997. Early-season applications of the fungus *Beauveria bassiana* and the introduction of the hemipteran predator Perillus biculatus for control of Colorado potato beetle. *Biol. Cont.* 10, 488–457.

SAS Institute Inc. 1999. SAS OnlineDoc®. Version 8. SAS Institute Inc. Cary, N.C.

Saxton, A. M., 1998. A macro for converting mean separation output to letter groupings in Proc Mixed. Proceedings 23rd SAS Users Group International. SAS Institute, Cary, pp. 1243–1246.

Schnepf, E., Crickmore, N., Van Rie, J., Lereclus, D., Baum, J., Feitelson, J., Zeigler, D. R. and Dean, D. H. 1998. *Bacillus thuringiensis* and its pesticidal crystal proteins. *Microbiol. Mol. Biol. Rev.* 62, 775–806.

Schroder, R. F. W., Martin, P. A. W. & Athanas, M. M. (2001). Effect of a phloxine B-cucurbitacin bait on diabroticite beetles (Coleoptera: *Chrysomelidae*). *J Econ Entomol* 94,892–897.

Sneath, P. H. A. 1984. Genus *Chromobacterium* Bergonzini. In "Bergey's Manual of Systematic Bacteriology". (D. H. Bergey, J. G. Holt, and N. R. Krieg, Eds), Vol 1. pp. 580–582. Williams & Wilkins, Baltimore.

Stackebrant, E. & Goebel, B. M. (1994). Taxonic note: a place for DNA—DNA reassociation and 16S rRNA sequence analysis in the present species definition in bacteriology. *Int J. Sys Bacteriol.* 44, 846–849.

Tailor, R., Tippett, J., Gibb, G., Pells, S., Pike, D., Jordan, L., and Ely, S. 1992. Identification and characterization of a novel *Bacillus thuringiensis* δ-endotoxin entomocidal to coleopteran and lepidopteran larvae. Mol. Microbiol. 6, 1211–1217.

Vazquez-Arista, M. Smith, R. H., Olalde-Portugal, V., Hinojosa, R. E., Hemandez-Delgadillo, R., Blanco-Labra, A. 1997. Cellulolytic bacteria in the digestive system of *Prostephanus truncatus* (Coleoptera: *Bostrichidae*). *J. Econ. Entomol.* 90, 1371–1376.

What is claimed is:

1. A biologically pure culture of a strain of *Chromobacterium subtsugae* sp. nov. having all the identifying characteristics of NRRL B-30655.

2. A biologically pure culture of a strain of *Chromobacterium subtsugae* sp. nov. which has the 16S rDNA gene sequence of SEQ ID NO:1.

3. A composition useful for control of insect pests, which comprises the strain of claim 1.

* * * * *